United States Patent [19]

Corey et al.

[11] Patent Number: 5,279,790

[45] Date of Patent: Jan. 18, 1994

[54] MEROCYANINE AND NITRO OR NITROSO SUBSTITUTED POLYHALOGENATED PHENOLSULFONEPHTHALEINS AS PROTEIN INDICATORS IN BIOLOGICAL SAMPLES

[75] Inventors: Paul F. Corey; Angela A. Michaels; Ronald G. Sommer, all of Elkhart, Ind.

[73] Assignee: Miles Inc., Elkhart, Ind.

[21] Appl. No.: 929,801

[22] Filed: Nov. 2, 1992

Related U.S. Application Data

[63] Continuation-in-part of Ser. No. 710,953, Jun. 6, 1991, abandoned.

[51] Int. Cl.$^5$ ............................................. G01N 21/00
[52] U.S. Cl. ................................................ 422/55–57; 436/169–170, 86, 436/810; 252/408.1

[58] Field of Search .................... 422/55–57; 436/169–170, 86, 810; 252/408.1

[56] References Cited

U.S. PATENT DOCUMENTS 4,013,416  3/1977  Rittersdorf et al. ............... 422/56
4,870,005  9/1989  Akiyoshi et al. .................. 422/55

Primary Examiner—Lyle A. Alexander
Attorney, Agent, or Firm—Roger N. Coe

[57] ABSTRACT

The present invention provides an analytical test strip for the detection of protein in a biological sample including a novel combination of protein error indicators. The invention includes, in combination, a partially halogenated phenolsulfonephthalein protein error indicator having nitro or nitroso substituent groups in the B and-/or C rings and a merocyanine protein error indicator.

18 Claims, 6 Drawing Sheets

MEROCYANINE AND NITRO OR NITROSO SUBSTITUTED POLYHALOGENATED PHENOLSULFONEPHTHALEINS AS PROTEIN INDICATORS IN BIOLOGICAL SAMPLES

BACKGROUND OF THE INVENTION

A. Related Application

This application is a continuation-in-part application of Ser. No. 710,953, filed Jun. 6, 1991 now abandoned.

B. Field Of The Invention

The present invention is related generally to the detection of protein; and more particularly, to a novel method for the determination of protein in a biological sample using novel protein error indicators.

C. Description Of The Background Art

Determining the presence of protein in a biological sample is of utmost importance in the diagnosis of several pathological conditions affecting the kidney, circulatory system, and central nervous system. Frequently, it is necessary to qualitatively and quantitatively measure protein (albumin) in urine. This is especially important in the diagnosis of diabetes and kidney disease. The predominant protein in diabetes is albumin; hence the model system for protein urine testing is albumin.

Methods for determining the presence of albumin in urine are well known. The most inexpensive and convenient method for albumin determination involves wetting a paper test strip with a small quantity of urine. The test strip is impregnated with a protein error indicator. If albumin is present in the sample, the test strip will indicate this by simply changing color. The color observed may vary depending on the concentration of albumin in the sample. This variable color change is used to quantify the albumin in the sample. Test papers of the above-type require a minimum of training to use correctly. These test strips provide an accurate, convenient and rapid vehicle for the on-the-spot determination of protein. Test papers such as these are widely used by technicians in clinical laboratories, as well as by physicians in their offices.

In more detail, these test strips include an absorbent carrier strip, i.e., paper, impregnated with a buffer, a polymer/surfactant (required for stability, wettability or to prevent leaching of the buffer) and a protein error indicator. Substantially all protein error indicators used in commercial dry phase tests are phenolsulfonephthalein derivatives sharing the basic structures below:

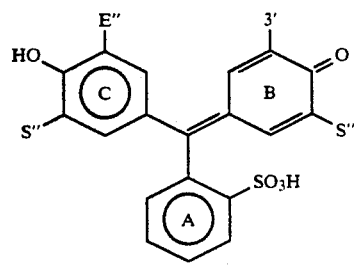

A

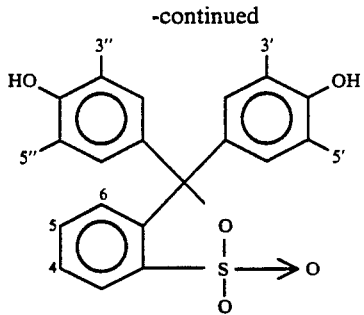

B

Structure A represents the general structure of phenolsulfonephthalein derivatives in protic solvents (water, alcohols, etc.) while structure B represents the form that predominates in the dry state or in aprotic solvents (ethers, acetonitrile, etc). Generally, phenolsulfonephthalein derived protein error indicators are represented as structure B. For purposes of consistency the protein error indicators of the present invention which are phenolsulfonephthalein derivatives will be represented using structure B. It should be understood, however, that the protein error indicators of the present invention which are phenolsulfonephthalein derivatives can also exist as structure A.

Protein error indicators are pH indicators including an ionizable group which has a pKa value that is displaced by the presence of protein. In the case of phenolsulfonephthaleins, the ionizable group is the C ring phenolic hydroxyl. The pKa value of a phenolsulfonephthalein indicator is the pH value at which one-half of the number of indicator molecules include deprotonated C ring phenolic hydroxyl group.

With regard to the phenolsulfonephthalein protein error indicators illustrated above, two deprotonation events occur in order to cause an observable color change. The first deprotonation removes the proton from the aryl sulfonic acid to yield the compound illustrated below:

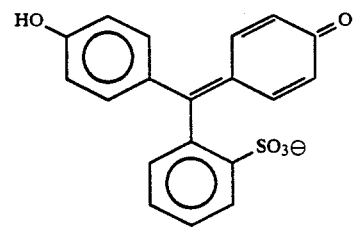

The pKa of this proton is less than one. Thus, this moiety is ionized at all useful pH values. This ionized group is also responsible for the aqueous solubility of these compounds.

The second deprotonation involves releasing a proton from the C ring phenolic hydroxyl to yield the dianion below:

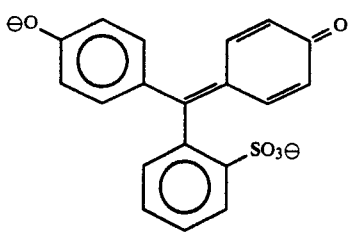

In protein error indicators, this second deprotonation causes the observable color change which is indicative of protein in the sample being tested.

The buffer provides the indicator an environment of constant pH in which to function. Thus, when the test strip is dipped into a biological fluid, which often has a significantly different pH value from the buffered environment, the indicator is not influenced by the pH of the biological fluid. This ensures that any subsequent color change in the indicator is a result of a shift in the indicator's pKa value and not a result of the pH of the sample being tested.

U.S. Pat. No. 4,870,005 mentions merocyanine as a dye for labelling. Specifically, the dye is chemically linked to an antigen (or antibody) for purposes of detection. There is no disclosure or suggestion of using merocyanine as a protein error indicator wherein advantage is taken of a color change that occurs when merocyanine interacts with protein.

Test strips which are generally considered useful for the analytical determination of protein in a biological sample are described in U.S. Pat. No. 4,013,416. The test strips described therein include an absorbent carrier impregnated with a water immiscible polypropylene glycol, a buffer and a protein error indicator of the octahalosulfophthalein group. The octahalosulfophthalein indicators are phenolsulfonephthalein derivatives halogenated at the 3',3",5',5"3,4,5, and 6 positions. According to the patent, test strips including octahalosulfophthalein and water immiscible polypropylene glycols are disturbed less by interfering nitrogen-containing compounds in the test sample than test strips including other phenolsulfonephthalein indicators and wetting agents. Nitro or nitroso substituted polyhalogenated phenolsulfonephthaleins are neither disclosed nor suggested by this patent.

Although the test strips described above are less disturbed by nitrogen-containing compounds in the sample, they and other presently available test strips suffer from several common serious disadvantages. Presently available test strips have background negative coloration which could lead to a misdiagnosis. For example, the indicators of the octahalosulfophthalein group are yellow colored in the absence of albumin. Subsequently, when albumin is added to the sample, the color changes from yellow to yellow-green to green, depending on the concentration of albumin in the sample. This background coloration is especially troublesome when it is considered that the biological fluid most often tested is urine which is normally colored yellow to yellow-green. Thus, the small change in the color of the test strip caused by trace amounts of albumin, i.e., from about 10 to 30 mg/dl (milligrams per deciliter) in urine could easily be masked by the color of the sample itself and go undetected. This problem is further compounded since these test strips are used by minimally trained technicians who may experience increased difficulty in interpreting the observed results. Because medical treatment is often initiated based on the results of these tests, the accurate interpretation of the results is imperative. Further, presently available test strips are not sensitive enough to detect very low levels of protein. Urinary albumin levels of from about 3 to about 10 mg/dl are significant in diagnosing several life threatening pathologies, such as diabetes and kidney disease. Nevertheless, test strips presently available cannot accurately detect albumin below about 10 mg/dl to 15 mg/dl.

Accordingly, to overcome the shortcomings discussed above, it would be extremely advantageous to provide a protein error indicator which is a color other than yellow in the absence of protein. It would provide an additional advantage if a protein error indicator was provided which presented one color other than yellow in the absence of protein and a second color clearly distinguishable from the first color in the presence of protein. It would be even more advantageous if the protein error indicator accurately and clearly indicated whether albumin was present as concentrations below those presently detectable. A still further advantage would be realized by providing a test strip including such a protein error indicator.

SUMMARY OF THE INVENTION

The present invention provides an analytical test strip for the detection of protein in a biological sample comprising an absorbent carrier impregnated with a nitro or nitroso substituted polyhalogenated phenolsulfonephthalein protein error indicator and a merocyanine protein error indicator.

In accordance with the invention, the above-described advantages are provided by an analytical test strip for the detection of protein in a biological sample comprising an absorbent carrier impregnated with the phenolsulfonephthalein protein error indicator compound:

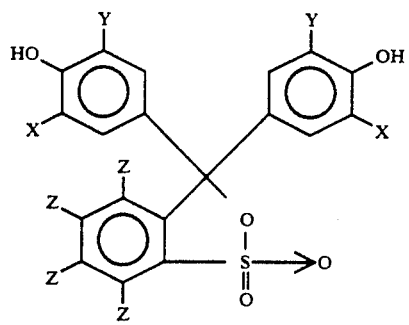

wherein:

X is —Cl, —Br, or —I,

Y is —NO$_2$ or —NO;

Z is —Cl, —Br, or —I; and the merocyanine protein error indicator compound:

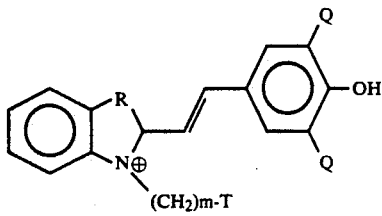

Q is —Cl, —Br, or —I;
m is an integer from 1 to 6;
R is S, Se, O or $C(C_nH_{2n+1})_2$, wherein n is an integer from 1 to 6; and T is —$SO_3^{\frac{1}{4}}$ or —H. In accordance with one embodiment of the invention X is —I, or —Br; Y is —$NO_2$; Z is —Br, or —Cl; Q is —Br or —I; m is 3 or 4; R is $C(CH_3)_2$; and T is —$SO_3^{\frac{1}{4}}$.

In accordance with a further aspect of the present invention, an analytical test strip is provided for the detection of protein in a biological sample comprising an absorbent carrier impregnated with the phenolsulfonephthalein protein error indicator compound:

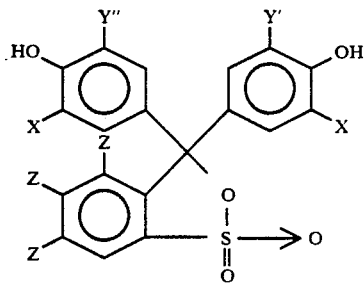

wherein:
X is —Cl, —Br, or —I;
Y' is —$NO_2$ or —NO;
Y" is —Cl, —Br, —I;
Z is —Cl, —Br, —I; and the merocyanine protein indicator compound:

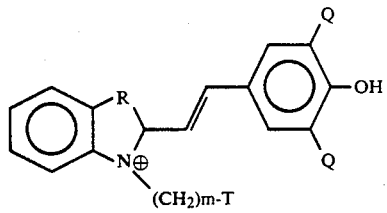

wherein:
Q is —Cl, —Br, or —I;
m is an integer from 1 to 6;
R is S, Se, O or $C(C_nH_{2n+1})_2$, wherein n is an integer from 1 to 6; and T is —$SO_3^{\frac{1}{4}}$ or —H. In accordance with one embodiment of the invention X is —I, or —Br; Y' is $NO_2$; Y" is —Cl or —Br; Z is —Br, or —Cl; Q is —Br or —I; m is 3 or 4; R is $C(CH_3)_2$; and T is —$SO_3^{\frac{1}{4}}$.

Another aspect of the present invention is directed to a method for the detection of protein in a biological sample. The method includes the step of wetting an analytical test strip with the biological sample. The test strip comprising an absorbent carrier impregnated with the protein error indicator compounds described above. The test strip is the observed to detect any color change. A color change is indicative of protein in the biological sample.

According to one embodiment of the invention the test strip is stabilized against heat stress. The protein assay (test strip) includes, for example, glycerol or sorbitol in addition to the color enhancing polymer, such as, polypropylene glycol, to provide heat stability. Also, it has been discovered that by replacing the standard citrate buffers used in protein assays with glycine thermal resistance is improved.

DESCRIPTION OF THE PREFERRED EMBODIMENTS

Figure 1:
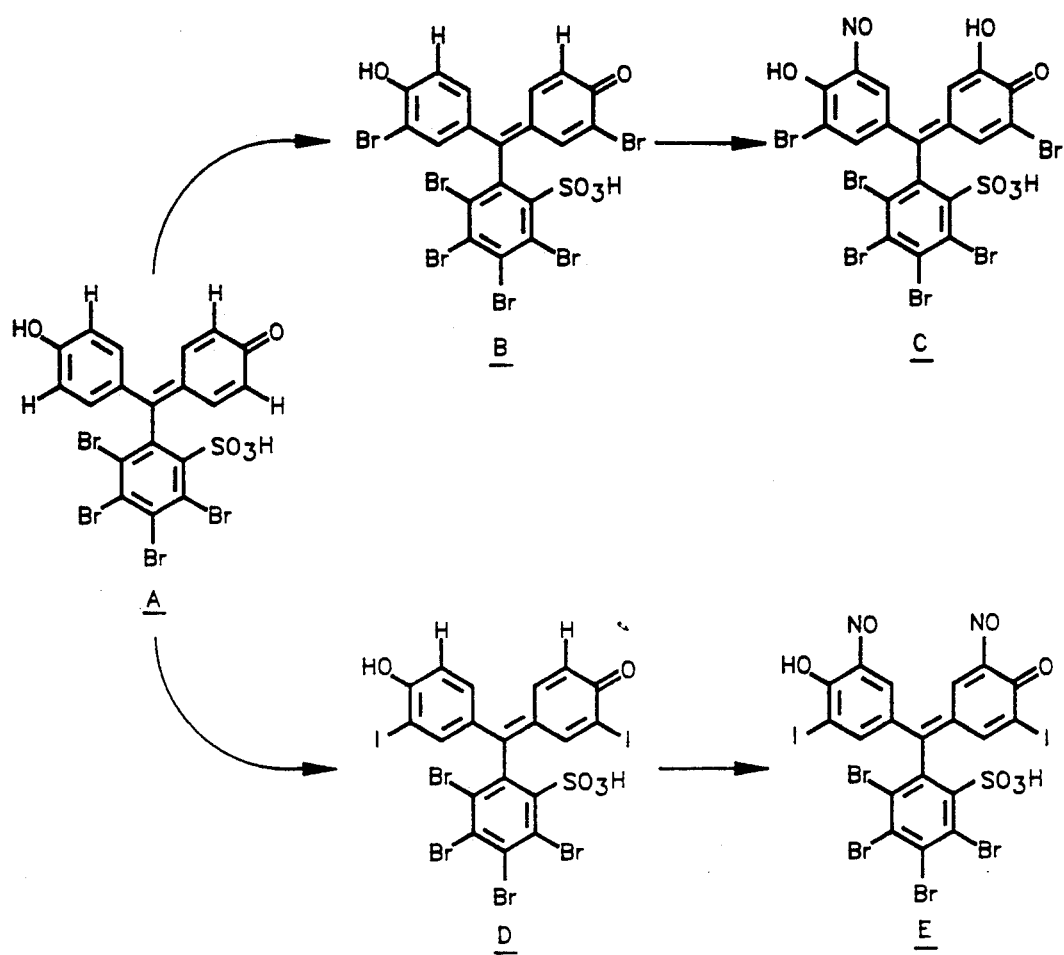
FIG. 1 is a schematic of processes for the synthesis of nitroso substituted polyhalogenated phenolsulfonephthalein protein error indicators.

In accordance with the invention, it has been discovered that test strips for the determination of protein in biological fluids having a significantly increased sensitivity to protein can be obtained by preparing an analytical test strip including the novel protein error indicators of the present invention.

Test strips including the below-described combination of novel protein error indicators are light peach, and on immersion into a biological sample containing protein become strongly colored green, blue, or purple, the color reflecting the concentration of protein in the sample. The green color produced is clearly distinct from the light peach of a negative test.

With reference to the observable color change from light peach to green, blue or purple, test strips prepared in accordance with the present invention are a diagnostic aid for the detection of protein in biological fluids by producing a different and distinct color in the presence of protein which is clearly distinguishable from the light peach of a negative test. This is distinguishable from other test strips which change slightly from one shade of a color to another in the presence of albumin, e.g., yellow to yellow-green. The characteristic of light peach for a negative test, and green, blue or purple in a positive test is seen as a significant departure from previous methods and indicators used to detect protein in biological samples. More specifically, the invention provides clinicians with a reliable, simple and accurate method for detecting protein in biological samples. The change from light peach to green, blue, or purple color makes the results of the test simple to interpret. This will result in less misdiagnosis, and accordingly, lower costs for the patient and health care provider.

Further, test strips prepared in accordance with the present invention positively detect a range of from about 2 to about 500 mg/dl of protein in a sample. Prior to the present invention, albumin concentrations of less than about 10 mg/dl were not accurately detectable. The detection of protein at these very low concentrations using the present invention makes possible the early diagnosis of several life threatening pathologies, including diabetes and kidney disease. For example, the detection of albuminuria at levels of 3 mg/dl and above will help clinicians to better diagnose diabetes in its early stages. In light of this significant advancement in the diagnosis of disease obtained with the present invention, the combination of protein error indicators in the test strips of the present invention provide a significant advancement in the art.

The present invention achieves the above-described significant advantages by providing a novel combination of protein error indicators in an analytical test strip for the detection of protein in a biological sample. The invention is directed to an analytical test strip including a partially halogenated phenolsulfonephthalein protein error indicator compound having nitro or nitroso substituent groups in the B and/or C rings, and a merocyanine protein error indicator. Until the present invention merocyanine dyes were unknown as protein error indicators. It is believed that the phenolsulfonephthalein protein error indicators of the invention are more sensitive to lower concentrations of albumin, while the merocyanine protein error indicators are more sensitive to higher concentrations of albumin. Thus, the reaction of these compounds with protein is not competitive, and accordingly, the effect of the novel combination is synergistic rather than additive.

In more detail, in accordance with one embodiment of the invention, the phenolsulfonephthalein protein error indicator of the present invention is the compound:

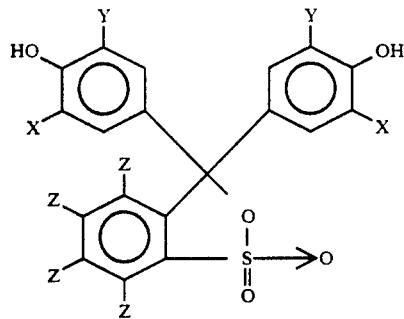

wherein: X is —Cl, —Br or —I; Y is —NO₂; or —NO; and Z is —Cl, —Br or —I. Preferably, X is —I, or —Br; Y is —NO₂; and Z is —Br or —Cl. More preferably, X is —I; Y is —NO₂; and Z is —Br.

In accordance with a further embodiment of the present invention, a phenolsulfonephthalein protein error indicator compound is provided which has the following formula:

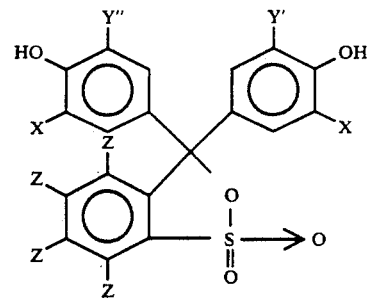

wherein: X is —Cl, —Br or —I; Y' is —NO₂ or —NO; Y" is —Cl, —Br or —I; and Z is —Cl, —Br or —I. More preferably, X is —I; Y' is —NO₂; Y" is —Br; and Z is —Br.

The merocyanine protein error indicator of the present invention is the compound:

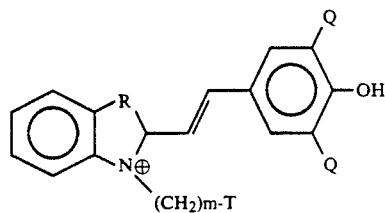

wherein: Q is —Cl, —Br or —I; m is an integer from 1 to 6; R is S, Se, O or C(C$_n$H$_{2n+1}$)₂, wherein n is an integer from 1 to 3; and T is is —SO₃¼ or —H. More preferably, Q is —Br or —I; m is an integer from 2 to 4; R is C(CH₃)₂; and T is —SO₃¼. Most preferably, Q is —I; and m is 3.

It should be understood that the present invention describes the first use of the merocyanine class of chromogens as protein error indicators and, accordingly, encompass a wide variety of substituted derivatives. It will be evident that the aromatic rings in the formula can bear a variety of substituent groups without departing from the scope of the present invention. Such substituent groups are limited only by the ability of one of ordinary skill in the art to prepare stable compounds which have the protein error indicator properties of the present invention, and include such groups as unsubstituted and substituted alkyl, unsubstituted and substituted aryl, alkoxy, aryloxy, halo (e.g., fluoro, chloro, bromo), nitro and substituted amino such as dialkylamino.

In the context of the present invention, "alkyl" is intended to include linear and branched forms of unsubstituted hydrocarbon residues of the general formula —C$_n$H$_{2n+1}$, preferably of the "lower alkyl" aliphatic type wherein n is 6 or less, such as methyl, ethyl, n-propyl, iso-propyl, n-butyl, iso-butyl, tert-butyl, n-hexyl, and the like, as well as substituted forms thereof.

Further, in the context of the present invention "aryl" is intended to include organic residues derived from an aromatic hydrocarbon ring or ring system by removal of a hydrogen atom, and include the unsubstituted hydrocarbon ring residues such as phenyl and naphthyl, and substituted forms thereof. For purposes of the present invention, aryl residues include those bearing one or more same or different functional groups or substituents which can be selected by one skilled in the art to provide the merocyanine protein error indicator compounds of the present invention.

More particularly, where "aryl" and "alkyl" are substituted, such substitution is intended to include such groups or substituents when mono- or polysubstituted with functional groups which do not substantially detract from the useful features of the present compounds. Such functional groups include chemical groups which may be introduced synthetically and result in the stable and useful merocyanine protein error indicator compounds of the present invention. Examples of such functional groups include, but are not intended to be limited to, halo (e.g., fluoro, chloro, bromo), substituted amino such as dialkylamino, nitro, alkoxy, aryloxy, alkyl, and aryl.

Illustrative merocyanine protein error indicators are: 1-(ω-sulfopropyl)-2-(4'-hydroxy-3',5'-dibromostyryl)-3,3-dimethylindoleninium betaine; 1-(ω-sulfobutyl)-2-(4'-hydroxy-3',5'-diiodostyryl)-benzothiazolium betaine; 1-(ω-sulfoethyl)-2-(4'-hydroxy-3',5'-diiodostyryl)-3,3-dimethylindoleninium betaine; 1-(ω-sulfopropyl)-2-(4'-hydroxy-3',5'-diiodostyryl)-3,3-dimethylindoleninum betaine; 1-(ω-sulfobutyl)-2-(4'-hydroxy-3',5'-diiodostyryl)-3,3-dimethylindoleninium betaine; and 1-(n-butyl)-2-(4'-hydroxy-3',5'-diiodostyryl)-3,3-dimethylindoleninium iodide. Detailed protocols for preparing the merocyanine protein error indicators listed above are set forth in the examples.

Referring to the figures, FIG. 1 generally illustrates the synthesis of two dinitroso-substituted indicators of the present invention. More specifically, FIG. 1 shows possible synthesis protocols for 3',3''-dinitroso-5',5'',3,4,5,6-hexabromophenolsulfonephthalein (compound C of FIG. 1) and 3',3''-dinitroso-5',5''-diiodo-3,4,5,6-tetrabromophenolsulfonephthalein (compound E of FIG. 1) from the commercially available 3,4,5,6-tetrabromophenolsulfonephthalein (compound A of FIG. 1). The dibromo-intermediate (compound B of FIG. 1) is readily prepared by treating a solution of tetrabromophenolsulfonephthalein in acetic acid (HOAc) with two equivalents of molecular bromine at ambient temperature. This is then nitrosylated in acetonitrile (CH$_3$CN) by an acid catalyzed reaction with isoamyl nitrite to afford 3',3''-dinitroso-5',5'',3,4,5,6-hexabromophenolsulfonephthalein.

The diiodo-analogs are prepared similarly. 3,4,5,6-tetrabromophenolsulfonephthalein is iodinated by reaction with a 3.0 equivalents of iodine monochloride (ICl) in HOAc at ambient temperature to give the compound illustrated as compound D in FIG. 1. This compound is then nitrosylated as above to afford 3',3''-dinitroso-5',5''-diiodo-3,4,5,6-tetrabromophenolsulfonephthalein. Following the above-described protocol, the synthesis of analogs including other halogens, alkyl groups or protons (H) at the positions 3',3'',3,4,5,5'',5'' or 6 is straightforward and yield the anticipated compounds.

Figure 2:
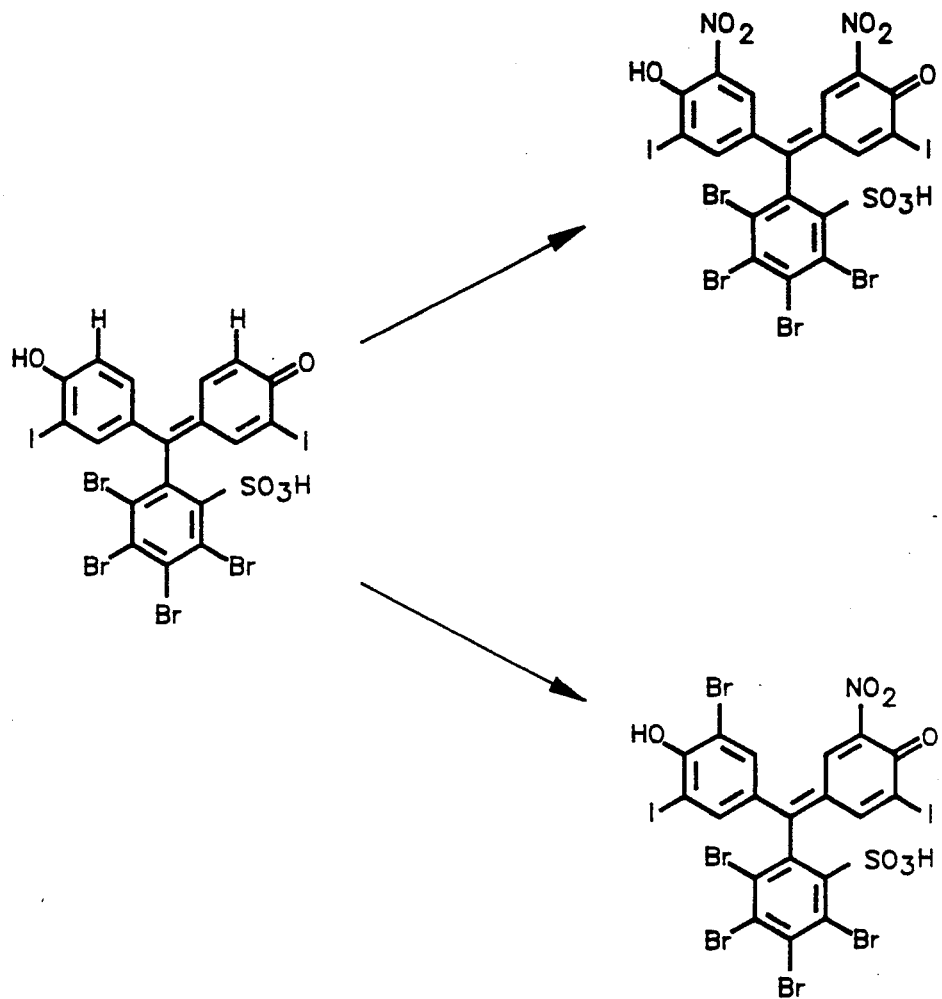
FIG. 2 is a schematic of processes for the synthesis of nitro substituted polyhalogenated phenolsulfonephthalein protein error indicators.

FIG. 2 generally illustrates the synthesis of the nitro-substituted protein error indicators of the present invention. Treatment of a solution of compound A of FIG. 2 in HOAc with no more than two equivalents of nitric acid (HNO$_3$) at ambient temperature affords 3',3''-dinitro-5',5''-diiodo-3,4,5,6-tetrabromophenolsulfonephthalein (compound B of FIG. 2). Slow treatment of compound A of FIG. 2 with one equivalent of HNO$_3$ in HOAc at ambient temperature followed by treatment with excess Br$_2$ at reflux give the mononitro-analog 3''-nitro-5',5''-diiodo-3,3',4,5,6-pentabromophenolsulfonephthalein (compound C of FIG. 2). Following the above-described protocol, the synthesis of analogs including other halogens, alkyl groups or protons (H) at the positions 3',3'',3,4,5,5'',5'' or 6 is straight-forward and yield the anticipated compounds. Described below in the Examples are detailed synthesis protocols for preparing each of the compounds illustrated in FIGS. 1 and 2.

Without limiting the invention, it is believed that the phenolsulfonephthalein protein error indicators included in the present invention account for the surprising protein sensitivity of the combination, more specifically, it is believed that the substitution of nitro or nitroso group(s) in the B and C rings is responsible for the increased sensitivity of these compounds to urinary albumin. It is believed that the phenomena of electron withdrawal and charge dispersal combine to provide indicators of increased sensitivity. It is also believed that the surprising characteristic of changing from light peach to green in the presence of very low concentrations of protein is attributable to the interaction of the two protein error indicators of the present invention.

In more detail, referring to the phenolsulfonephthalein protein error indicators of the present invention, it is believed that the highly electronegative nitro or nitroso groups, situated adjacent to the hydroxyl groups at the 4' and 4'' positions, increase the reactivity of those hydroxy groups. In addition, it is also believed that the reactivity of the hydroxyl groups is further enhanced through resonance stability. It is believed that ionic forms of the molecule are stabilized through charge dispersal. The resonance stability imparted by the substituent nitro and nitroso groups increases the acidity of the adjacent hydroxyl hydrogen at the 4' and 4'' positions. These phenomena combine, synergistically it is believed, to reduce the pKa of the phenolsulfonephthalein indicators of the present invention, and accordingly, increase the sensitivity of the invention combination indicator to albumin.

FIGS. 3-8 generally illustrate the synthesis of several merocyanine protein indicator compounds of the present invention. The chemistry is straight forward and generally involves the coupling of an aromatic hydroxyaldehyde with a heterocyclic quartenary salt under basic reaction conditions. The general procedures used in preparing the merocyanine protein error indicators are illustrated in FIGS. 3-8 and are discussed in detail in the examples below.

One aspect of the present invention is directed to an analytical test strip for the detection of protein in a biological sample comprising an absorbent carrier impregnated with one of the phenolsulfonephthalein protein error indicator compounds described above and one of the merocyanine protein error indicator compounds described above. The absorbent carrier of the test strip is preferably a filter paper. Other materials useful as the absorbent carrier include felt, porous ceramic strips, and woven or matted glass fibers described in U.S. Pat. No. 3,846,247. Also suggested are the use of wood, cloth, sponge material and argillaceous substances (described in U.S. Pat. No. 3,552,928). Alternatively, the absorbent carrier can be nonporous, such as various polymeric films, glass and the like. All such absorbent carrier materials are feasible for use in the present invention, as are others. It has been found, however, that filter paper is especially suitable.

The absorbent strip is preferably impregnated with a buffer. Any buffer system which can be adjusted to a pH of from about 1.5 to about 4.5 is useful in the practice of the present invention. Preferably, the buffer system is adjusted to a pH of about 2.0 to about 3.0, and most preferably about 2.5.

The test strip can also be impregnated with a color enhancing polymer. For purposes of the present invention, the term "color enhancing polymer" is intended to mean a polymer having a molecular weight from about 400 to about 25,000 which increases both the kinetics of the color formation and the dose response of the protein error indicators and/or reduced background color for a negative test. Preferred color enhancing polymers include polypropylene glycols, polycarbonates, polyvinyl ethers and polyethylene oxides. According to one preferred embodiment, the color enhancing polymer is a polypropylene glycol. Both water miscible and immiscible polypropylene glycols are useful in the practice of the present invention. It is preferred that the polypropylene glycol has a molecular weight of from about 100 to 10,000. More preferably, the polypropylene glycol has a molecular weight of from about 1,000 to about 4,000. Most preferably, however, the polypropylene glycol has a molecular weight of about 2,000. Water immiscible polypropylene glycols useful in the practice of the present invention are discussed in detail in U.S. Pat. No. 4,013,416. Nevertheless, it has been determined that water miscible polypropylene glycols having an average molecular weight of about 400 are useful in the practice of the present invention. Other preferred color enhancing polymers include: a carbonate copolymer having an average molecular weight of 1594 which has tradename designation of KOK 10,071 from Bayer AG, Germany; a polypropylene oxide and ethylene oxide adduct or 1,6-dimethyl-4-nonyl-phenol available under the tradename designation of Fenoil D4030 from Bayer AG, Germany; and a polyvinylmethylether available under the tradename designation Lutonal M40 from BASF, USA. It has been determined that test strips of the present invention which include certain color enhancing polymers, i.e., polypropylene glycols, KOK 10,071, Fenoil D4030 and Lutonal M40, have an increased dose response range, an increased resolution between albumin levels and a decreased negative coloration.

Specifically, KOK 10,071 is a propylene oxide carbonate copolymer prepared by the Titanium (IV) butoxide catalyzed condensation of Polyether L 950 ® (Bayer AG) with diphenyl carbonate. The starting material Polyether L 950 is a difunctional polypropylene glycol with a number average molecular weight of 423, prepared by polymerizing propylene oxide in the presence of 1,2-propanediol. A polymer chain grows off of each of the diol residues, resulting in a linear polyether with each end terminating in a secondary hydroxyl group (i.e., a hydroxyl group functionality of two). The KOK 10,071 copolymer results from the connection of polyether residues with carbonate linkages in the following proportions:

|  | amt (g) | amt (mol) |
|---|---|---|
| Polyether L 950 | 4248 | 10.22 |
| Diphenyl Carbonate | 1581 | 7.39 |
| Ti(OC$_4$H$_9$)$_4$ | 0.6 | 0.0018 |

The following examples are presented to describe preferred embodiments and utilities of the present invention and are not meant to limit the present invention unless otherwise stated in the claims appended hereto.

EXAMPLES

Example 1

3',3'',3,4,5,6-Hexabromophenolsulfonephthalein

A solution of 3,4,5,6-tetrabromophenolsulfonephthalein, obtained from the Aldrich Chemical Co., Milwaukee, Wis., USA, [5.03 g (grams), 7.5 mmole (millimoles)] in acetic acid [(HOAc, 50 ml (milliliters)] was maintained at ambient temperature under an inert gas atmosphere. The solution was dropwise treated for 10 minutes with a solution of bromine, obtained from the Aldrich Chemical Company, (2.4 g, 15 mmol, in HOAc, 10 ml), and thereafter stirred overnight. The solids that separated from the reaction mixture were collected by filtration, washed with HOAc and dried in vacuo to provide 3',3'',3,4,5,6-hexabromophenolsulfonephthalein. Recrystallization from boiling HOAc provided the analytically pure compound (1.93 g, 29.3%) as a pale pink powder which softened at 159°-160° C., melted with gas evolution at 162°-164° C. and then resolidified with no melting point below 270° C. Spectroscopic data identifying the compound are set forth in Table 1.

Table 1

IR (KBr) cm$^{-1}$ 3435, 1703, 1605, 1497, 1416, 1360, 1340, 1295, 1227, 1192.

$^1$H NMR (DMSO-d$^6$)δ 8.03 (s, 2H), 7.59 (d, J=2.4 Hz, 2H), 7.31 (d of d, J$_1$=8.7 Hz and J$_2$=2.4 Hz, 2H), 7.11 (d, J=8.7 Hz, 2H).

Analysis calculated for C$_{19}$H$_8$Br$_6$O$_5$S·HOAc: C, 28.90; H, 1.39. Found: C, 28.55; H, 1.38.

Example 2

5',5''-Dinitroso-3',3'',3,4,5,6-Hexabromophenolsulfonephthalein

A stirred solution of 3',3'',3,4,5,6-hexabromophenolsulfonephthalein (0.67 g, 0.8 mmole) in anhydrous acetonitrile (CH$_3$CN, 50 ml) was maintained at an ambient temperature under an inert gas atmosphere. The solution was treated with a catalytic amount of HOAc (one drop) and isoamyl nitrite (0.56 g, 4.8 mmole), and thereafter stirred for 4 days. The solids that separated from the reaction mixture were collected by filtration, and washed with CH$_3$CN (10 ml). The solid was dried in vacuo to afford 5',5''-dinitroso-3',3'',3,4,5,6-hexabromophenolsulfonephthalein (0.45 g, 64%) as an analytically pure yellow powder with a melting point of 267°-269° C. A second crop was subsequently obtained from the concentrated mother liquors (0.03 g; 4%). Spectroscopic data identifying the compound are set forth below in Table 2.

Table 2

IR (KBr) cm$^{-1}$ 1621, 1543, 1468, 1416, 1361, 1341, 1325, 1258, 1194, 1162, 1096.

$^1$H NMR (DMSO-d$^6$)δ 7.93 (d, J=2.5 Hz, 2H), 7.73 (d, J=2.5 Hz, 2H), 4.20 (v. br. s, 2H).

Analysis calculated for C$_{19}$H$_6$Br$_6$N$_2$O$_7$S: C, 25.76; H, 0.68; N, 3.16. Found: C, 25.61; H, 0.58; N, 3.40.

Example 3

3',3''-Diiodo-3,4,5,6-Tetrabromophenolsulfonephthalein 3,4,5,6-tetrabromophenolsulfonephthalein (20.1 g, 30 mmole) was dissolved in 70° C. HOAc (550 ml) then cooled to ambient temperature in a water bath. The stirred solution was maintained under an inert gas atmosphere. The solution was treated with a solution of iodine monochloride (ICl) (14.61 g, 90 mmole) in HOAc (50 ml) and left at ambient temperature for 22.3 hours. The reaction mixture was filtered through a pad of Celite 521 (Johns-Manville Corp., Denver, Colo., USA), and evaporated to dryness in vacuo. The resulting red tar was taken up in HOAc (150 ml). The solids which separated from this solution on standing were filtered, washed with HOAc and dried in vacuo to afford 3',3''-diiodo-3,4,5,6-tetrabromophenolsulfonephthalein (9.66 g, 34.9%) as a pink powder. A second crop was subsequently obtained from the concentrated mother liquors (4.03 g, 14.6%). Spectroscopic data identifying the compound are set forth below in Table 3.

Table 3

IR (KBr) cm$^{-1}$ 1697, 1598, 1486, 1405, 1338, 1293, 1226, 1191.

$^1$H NMR (DMF-d$^7$)δ 8.03 (s, 2H), 7.97 (d, J=2.3 Hz, 2H), 7.49 (d of d, J$_1$=8.6 Hz and J$_2$=2.3 Hz, 2H), 7.02 (d, J=8.6 Hz, 2H).

Analysis calculated for C$_{19}$H$_8$Br$_4$I$_2$O$_5$S·HOAc: C, 25.69; H, 1.23. Found: C, 25.94; H, 0.94.

Example 4

5',5''-Dinitroso-3',3''-Diiodo-3,4,5,6-Tetrabromo-phenolsulfonephthalein

A solution of 3',3''-diiodo-3,4,5,6-tetrabromophenolsulfonephthalein (1.47 g, 1.6 mmole) in anhydrous CH$_3$CN (50 ml) was maintained at ambient temperature under an inert gas atmosphere. The mixture was thereafter treated with a catalytic amount of HOAc (2 drops) and isoamyl nitrite (2.3 g, 20 mmole). The resulting mixture was allowed to stir for two days. The solids that separated from the reaction mixture were collected by filtration, washed with cold CH$_3$CN and dried in vacuo to give the compound 5',5''-dinitroso-3',3''-diiodo-3,4,5,6-tetrabromophenolsulfonephthalein (0.41 g, 26%). Recrystallization from CH$_3$CN (150 ml) resulted in providing the analytical sample as a pale yellow wool with no melting point below 270° C. Spectroscopic data identifying the compound are set forth below in Table 4.

Table 4

IR (KBr) cm$^{-1}$ 1616, 1541, 1460, 1410, 1360, 1322, 1257, 1195, 1091.

$^1$H NMR (DMSO-d$^6$)δ 8.00 (d of d, J$_1$=2.0 Hz and J$_2$=1.2 Hz, 2H), 7.93 (d, J=2.2 Hz, 2H), 4.76 (v. br. s, 2H).

Analysis calculated for C$_{19}$H$_6$Br$_4$I$_2$N$_2$O$_7$S: C, 22.93; H, 0.46; N, 2.80. Found: C, 23.08; H, 0.71; N, 2.83.

Example 5

5',5''-Dinitro-3',3''-Diiodo-3,4,5,6-Tetrabromophenol-sulfonephthalein (DIDNTB)

A stirred solution 3',3''-diiodo-3,4,5,6-tetrabromophenolsulfonephthalein (1.85 g, 2.0 mmole) in boiling HOAc (90 ml ) was cooled to about 16°-20° C. The solution was dropwise treated, over four minutes, with a solution of 90% nitric acid (0.28 g, 4.0 mmole) in HOAc (10 ml) and left to stir overnight at ambient temperature under an inert gas atmosphere. The solids that separated from the reaction mixture were collected by filtration washed with HOAc (5 ml) and dried in vacuo to afford a crude preparation of 5',5''-dinitro-3',3''-diiodo-3,4,5,6-tetrabromophenolsulfonephthalein. One recrystallization from HOAc (110 ml) provided the analytically pure compound 5',5''-dinitro-3',3''-diiodo-3,4,5,6-tetrabromophenolsulfonephthalein (0.90 g, 38%) as a yellow powder. This material had no distinct melting point. However, the material shrunk at about 189°-190° C., evolved gas at about 210°-220° C. and melted at about 225° C. Spectroscopic data identifying the compound are set forth below in Table 5.

Table 5

IR (KBr) cm$^{-1}$ 1707, 1616, 1541, 1460, 1408, 1370, 1322, 1257, 1195, 1092.

$^1$H NMR (DMSO-d$^6$)δ 8.03 (d, J=2.4 Hz, 2H), 7.91 (d, J=2.4 Hz, 2H), 6.0-7.0 (br. s, 2H).

Analysis calculated for C$_{19}$H$_6$N$_2$Br$_4$I$_2$O$_9$S·2HOAc: C, 24.40; H, 1.25; N, 2.48. Found: C, 24.49; H, 1.00; N, 2.42.

Example 6

5'-Nitro-3',3''-Diiodo-5'',3,4,5,6-Pentabromophenolsulfonephthalein

A stirred solution of 3',3''-diiodo-3,4,5,6,-tetrabromophenolsulfonephthalein (0.92 g, 1.0 mmole) in boiling HOAc was cooled to ambient temperature, and maintained under an inert gas atmosphere. The solution was slowly treated dropwise, over 1.5 hours, with 1M HNO$_3$ in HOAc (1.05 ml; 1.05 mmole). Once the addition was complete, the reaction was allowed to stir for five minutes. Thereafter the reaction mixture was treated with a solution of Br$_2$ in HOAc (1.5 ml, 1.5 mmole) and refluxed for 5.5 hours. The mixture was thereafter cooled to ambient temperature and evaporated to dryness in vacuo to afford a golden-brown glass (1.10 g). The crude product was taken up in a minimum volume of ethyl acetate (EtOAc) and diluted with HOAc to provide a crystalline solid. After two recrystallizations there was obtained analytically pure 5'-nitro-3',3''-diiodo-5'',3,4,5,6-pentabromophenolsulfonephthalein (0.57 g, 54.5%) as a bright yellow powder. Spectroscopic data identifying the compound are set forth below in Table 6.

Table 6

IR (KBr) cm$^{-1}$ 1708, 1614, 1540, 1462, 1406, 1371, 1338, 1324, 1252, 1194, 1162, 1091, 1016, 823, 789, 765, 723, 671.

$^1$H NMR (DMSO-d$^6$)δ 8.03 (d of d, J$_1$=24.8 Hz and J$_2$=2.3 Hz, 2H), 7.98 (d of d, J$_1$=22.7 Hz, and J$_2$=2.4 Hz, 1H), 7.90 (br. m, 1H), 7.67 (br. m, 1H).

Analysis calculated for C$_{19}$H$_6$Br$_4$I$_2$NO$_7$S; C, 21.82; H, 0.58; N, 1.34. Found: C, 22.16; H, 0.33; N, 1.33.

Example 7

Figure 3:
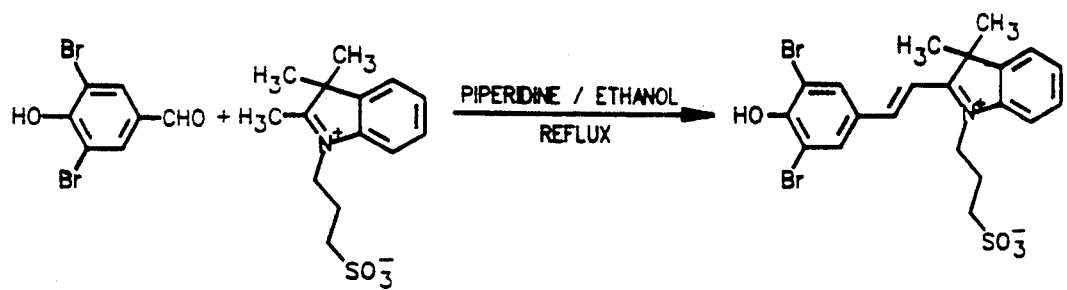
FIGS. 3–8 are schematics of processes for the synthesis of merocyanine protein error indicators.

1-(ω-Sulfopropyl)-2-(4'-Hydroxy-3',5'-Dibromostyryl)-3,3-Dimethylindoleninium Betaine A solution of 3,5-dibromo-4-hydroxybenzaldehyde (Lancaster Synthesis, Ltd., Windham, N.H., USA) (2.0 g, 7.14 mmol), 1-(ω-sulfopropyl)-2,3,3-trimethylindoleninium betaine (Belg. 726,639; CA 73:P82538a) (2.0 g, 7.11 mmole) and piperidine (0.4 ml) in EtOH (30 ml) was maintained under an inert gas atmosphere. The solution was refluxed for 50 minutes and cooled in an ice bath. The reaction mixture was evaporated to dryness in vacuo, and taken up in a minimum of methanol (MeOH). The solution was thereafter chromatographed on silica gel (600 grams) using MeOH/CHCl$_3$ (1:4 v/v) development. Fractions containing the major purple product band were pooled and acidified with excess HCl in 2-propanol (i-PrOH) to produce the color change from purple to golden yellow. The solution was evaporated to dryness in vacuo. The residue was take up on hot EtOH (ca. 25 ml) and crystallized upon cooling. The solids that separated were collected by filtration, washed with ice-cold EtOH/hexane (3:1 v/v), and vacuum dried to give the analytically pure compound 1-(ω-sulfopropyl)-2-(4'-hydroxy-3',5'-dibromostyryl)-3,3-dimethylindoleninium betaine (0.96 g, 25%) as golden yellow crystals. The compound had no distinct melting pot, but darkened at temperatures above 200° C. The above-described method for preparing the compound is generally illustrated by FIG. 3. Spectroscopic data identifying the compound are set forth below in Table 7.

Table 7

IR (KBr) cm$^{-1}$ 3438, 3055, 1606, 1577, 1519, 1475, 1406, 1372, 1305, 1277, 1212, 1173, 1124, 739.

$^1$H NMR (DMSO-d$^6$)δ 8.58 (s, 2H), 8.29 (d, J=16.0 Hz, 1H), 7.97 (d, J=7.7 Hz, 1H), 7.84 (d of d, J$_1$=2.0 Hz and J$_2$=6.6 Hz, 1H), 7.67 (d, J=16 Hz, lH), 7.54-7.64 (m, 2H), 4.81 (t, J=7.6 Hz, 2H), 3.77 (v. br. s, 1H), 2.63 (t, J=6.6 Hz, 2H), 2.10-2.22 (m, 2H), 1.76 (s, 6H).

$^{13}$C NMR (DMSO-d$^6$)ppm 181.6, 155.6, 151.3, 143.8, 140.9, 135.1, 129.2, 129.1, 128.7, 123.0, 115.2, 112.5, 111.6, 52.2, 47.3, 45.5, 25.6, 24.8 (3 coincident bands).

Analysis calculated for C$_{21}$H$_{21}$Br$_2$NO$_4$S·½ EtoH: C, 46.65; H, 4.27; N, 2.47. Found: C, 46.48; H, 4.50; N, 2.33.

Example 8

1-(ω-Sulfobutyl)-2-(4'-Hydroxy-3',5'-Diiodostyryl)-Benzothiazolium Betaine

Figure 4:
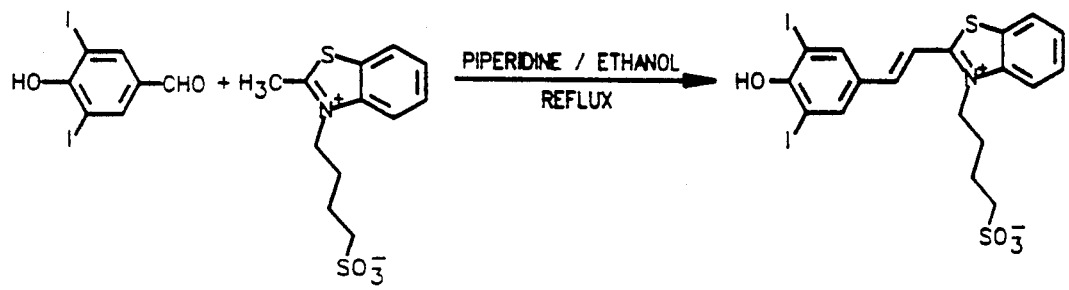

A mixture of 3,5-diiodo-4-hydroxybenzaldehyde (Lancaster Synthesis, Ltd. Windham, N.H., USA) (3.74 g, 10 mmole), 3-(ω-sulfobutyl)-2-methylbenzothiazolium betaine (Brit. 742,112; CA 50:P11149e) (3.71 g, 13 mmole) and piperidine (0.8 ml) in EtOH (30 ml) was maintained under an inert gas atmosphere. The solution was refluxed for one hour then cooled to ambient temperature. The reaction mixture was acidified with sufficient 1.93M hydrochloric acid in i-PrOH to effect a color change from purple to yellow whereupon solids separated from the solution. The solids were collected by filtration, washed with EtOH and dried. The solids were then dissolved in warm (55° C.) EtOH/MeOH/H$_2$O (3:2:1 v/v/v) (300 ml) containing 2M aqueous sodium hydroxide (5.2 ml), filtered through celite (Johns-Manville Corp., Denver, Colo., USA) and precipitated by the addition of 3M aqueous hydrochloric acid (6 ml). After cooling in an ice bath, the solids were collected by filtration, washed with EtOH and dried in vacuo. The solids were then boiled in acetic acid (HOAc) (600 ml), filtered and dried in vacuo at 115° C. to provide the analytically pure compound 1-(ω-sulfobutyl)-2-(4'-hydroxy-3',5'-diiodostyryl)-benzothiazolium betaine (5.10 g, 79%) as a yellow powder. The above-described method for preparing the compound is generally illustrated by FIG. 4. Spectroscopic data identifying the compound are set forth below in Table 8.

Table 8

IR(KBr) cm$^{-1}$ 3436, 1608, 1572, 1529, 1497, 1458, 1396, 1318, 1267, 1208, 1038.

$^1$H NMR (DMSO-d$^6$)δ 8.55, (s, 1H), 8.30-8.50 (m, 3H), 7.92-8.16 (m, 3H), 7.73-7.88 (m, 2H), 4.95 (br. t, J=7.5 Hz, 2H), 2.53 (t, J=7.1 Hz, 2H), 1.98 (br. m, 2H), 1.81 (q, J=7.0 Hz, 2H).

$^{13}$C NMR (DMSO-d$^6$)ppm 171.4, 159.1, 148.1, 146.1, 141.0, 140.6, 131.5, 129.2, 128.0, 123.9, 116.7, 112.2, 86.4, 50.0, 48.8, 27.2, 21.9 (2 coincident bands).

Analysis calculated for C$_{19}$H$_{17}$I$_2$NS$_2$O$_4$: C, 35.58; H, 2.67; N, 2.18. Found: C, 35.52; H, 2.75; N, 2.06.

Example 9

Figure 5:
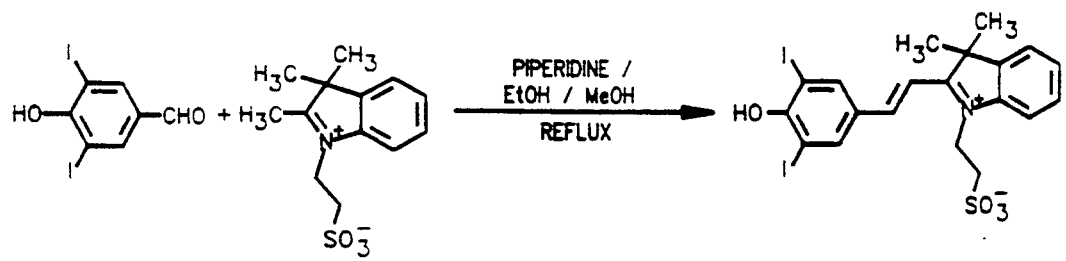

1-(ω-Sulfoethyl)-2-(4'-Hydroxy-3',5'-Diiodostyryl)-3,3-Dimethylindoleninium Betaine A mixture of 3,5-diiodo-4-hydroxybenzaldehyde (3.73 g, 10 mmole), 1-(ω-sulfoethyl)-2,3,3-trimethylindoleninium bromide (U.S. Pat. No. 2,503,776; CA 44:P5738i) (6.61 g; 19 mmole) and piperidine (2.0 ml) in EtOH/MeOH (2:1 v/v) (60 ml) was maintained under an inert gas atmosphere. The solution was refluxed for 4 hours, cooled to an ambient temperature, and evaporated to dryness in vacuo leaving a brown residue. The brown residue was taken up in MeOH (2-3 ml). This solution was treated with triethylamine (NET$_3$) (2 ml) and chromatographed on silica gel using MeOH/CHCl$_3$ (1:4 v/v) development. The fractions containing the purple product band were pooled and evaporated to dryness in vacuo. This crude product was taken up in EtOH (10 ml), acidified with sufficient 1.93 M HCl in i-PrOH to effect a color change from purple to yellow. This solution was evaporated to dryness. The residue was then taken up in EtOH/hexane (3:1 v/v), and refrigerated until the solution crystallized. The crystalline solids that separated were collected by filtration. These solids were washed with ice-cold EtOH and then EtOH/hexane. The remaining solids were vacuum dried to give the compound 1-(ω-sulfoethyl)-2-(4'-hydroxy-3',5'-diiodostyryl)-3,3-dimethylindoleninium betain (0.80 g; 12.8%). Recrystallization from EtOH/HOAc provided the analytically pure compound as a dark reddish-brown powder. The above-described method for preparing the compound is generally illustrated by FIG. 5. Spectroscopic data identifying the compound are set forth below in Table 9.

Table 9

IR (KBr) cm$^{-1}$ 3444, 2992, 1608, 1574, 1530, 1469, 1399, 1371, 1327, 1296, 1282, 1230, 1212, 1178, 1141, 1086, 1033, 964.

$^1$H NMR (DMSO-d$^6$)δ 5 8.58 (s, 2H), 8.18 (d, J=16.3 Hz, 1H), 7.69-7.88 (m, 4H), 7.51-7.62 (m, 2H), 4.82 (t, J=5.7 Hz, 2H), 3.04 (t, J=6.1 Hz, 2H), 1.73 (s, 6H);

$^{13}$C NMR (DMSO-d$^6$)ppm 182.4, 160.0, 149.1, 143.6, 141.4, 140.7, 130.5, 128.8, 122.8, 115.1, 112.9, 87.3, 52.0, 47.7, 43.7, 25.4 (4 coincident bands).

Analysis calculated for C$_{20}$H$_{19}$I$_2$NO$_4$S·¼EtOH: C, 39.02; H, 3.43; N, 2.16. Found: C, 39.25; H, 3.47; N, 2.2.

EXAMPLE 10

1-(ω-Sulfopropyl)-2-(4'-Hydroxy-3',5'-Diiodostyryl)-3,3-Dimethylindoleninium Betaine (SPDIB)

Figure 6:
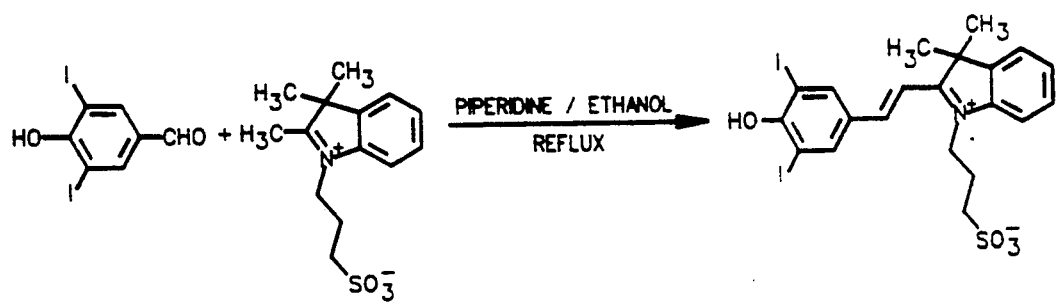

A mixture of 3,5-diiodo-4-hydroxybenzaldehyde (3.73 g, 10 mmole), 1-(ω-sulfopropyl)-2,3,3-trimethylindoleninium betaine (3.65 g, 13 mmole) and piperidine (0.8 ml) in EtOH (ca. 50 ml) was maintained under an inert gas atmosphere. The solution was refluxed for 2.75 hours and then cooled in an ice bath. The solution was acidified with 1.93M HCl in i-PrOH (5.0 ml). A dark tar separated and was collected by filtration and triturated with boiling HOAc. The combined triturates were evaporated in dryness in vacuo, taken up in HOAc (20 ml) and allowed to crystallize. The solids that separated were collected by filtration, washed with HOAc and vacuum dried to give the compound 1-($\omega$-sulfopropyl)-2-(4'-hydroxy-3',5'-diiodostyryl)-3,3-dimethylindoleninium betaine (4.37 g, 68%) as an orange powder. The compound was recrystallized from HOAc to provide the analytically pure compound. The above-described method for preparing the compound is generally illustrated by FIG. 6. Spectroscopic data identifying the compound are set forth below in Table 10.

Table 10

IR (KBr) cm$^{-1}$ 1604, 1572, 1526, 1468, 1402, 1376, 1274, 1214, 1173, 766, 722.

$^1$H NMR (DMSO-d$^6$)$\delta$ 8.71 (s, 2H), 8.21 (d, J=15.5 Hz, 1H), 7.92 (d, J=7.2 Hz, 1H), 7.81 (d, J=6.6 Hz, 1H), 7.50-7.65 (m, 3H), 4.72-4.82 (v. br. m, 2H), 3.57 (v. br. s, 1H), 2.61 (t, J=6.5 Hz, 2H), 2.07-2.20 (v. br. m, 2H) 1.76 (s, 6H).

$^{13}$C NMR (DMSO-d$^6$)ppm 181.3, 160.6, 151.1, 143.7, 142.0, 140.9, 130.0, 129.1, 122.9, 115.0, 110.7, 87.4, 52.0, 47.3, 45.4, 25.7, 24.7 (4 coincident bands).

Analysis calculated for C$_{21}$H$_{21}$I$_2$NO$_4$S·½H$_2$O: C, 39.02; H, 3.43; N, 2.17. Found: C, 39.01, H, 3.46; N, 1.94.

Example 11

Figure 7:
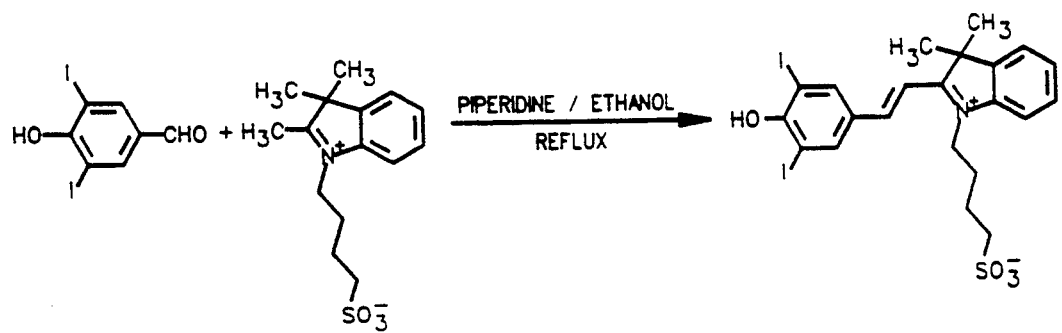

1-($\omega$-Sulfobutyl)-2-(4'-Hydroxy-3',5'-Diiodostyryl)-3,3-Dimethylindoleninium Betaine A mixture of 3,5-diiodo-4-hydroxy-benzaldehyde (1.87 g, 5 mmol), 1-($\omega$-sulfobutyl)-2,3,3-trimethylindoleninium betaine [R. B. Majumdar et al., *Cytometry* 10:11-9 (1989)] (2.36 g, 8 mmole) and piperidine (0.4 ml) in EtOH (35 ml) was maintained under an inert gas atmosphere. The solution was refluxed for 2.5 hours and then cooled to an ambient temperature. The reaction mixture was acidified with an excess of 1.93M HCl in i-PrOH, and evaporated to dryness in vacuo, leaving a residue. The residue was taken up in EtOH (10 ml). On standing in a refrigerator, solids separated from the mixture. The solids were collected by filtration, washed with ice-cold EtOH/hexane (3:1 v/v), and vacuum dried to afford an orange solid (3.36 g). The crude product was taken up in boiling EtOH (ca. 30 ml) and immediately reprecipitated. Additional boiling EtOH was added, (ca. 200 ml) but the solid did not redissolve. After cooling in ice the solids were collected by filtration, washed with EtOH and vacuum dried to provide the analytically pure compound (1-($\omega$-sulfobutyl)-2-(4'-hydroxy-3',5'-diiodostyryl)-3,3-dimethylindoleninium betaine (1.54 g, 47%) as an orange powder. The above-described method for preparing the compound is generally illustrated by FIG. 7. Spectroscopic data identifying the compound is set forth below in Table 11.

Table 11

IR (KBr) cm$^{-1}$ 2977, 1605, 1572, 1525, 1469, 1401, 1372, 1308, 1271, 1214, 1182, 1120, 1034, 769, 714.

$^1$H NMR (DMSO-d$^6$)$\delta$ 8.71 (s, 2H), 8.24 (d, J=16.0 Hz, 1H), 7.90-7.97 (m, 1H), 7.81-7.87 (m, 1H), 7.53-7.64 (m, 3H), 4.68 (t, J=7.2 Hz, 2H), 2.45-2.55 (m, 2H), 1.89-2.00 (m, 2H), 1.75-1.83 (m, 2H), 1.76 (s, 6H).

$^{13}$C NMR (DMSO-d$^6$)ppm 181.3, 160.5, 151.1, 143.7, 141.9, 140.8, 130.0, 129.0, 122.9, 115.2, 110.7, 87.3, 52.0, 50.3, 46.2, 27.2, 25.8, 22.3 (4 coincident bands).

Analysis calculated for C$_{22}$H$_{23}$I$_2$NO$_4$S: C, 40.57; H, 3.56; N, 2.15. Found: C, 40.59; H, 3.50; N, 1.99.

Example 12

1-(n-Butyl)-2-(4'-Hydroxy-3',5'-Diiodostyryl)-3,3-Dimethylindoleninium Iodide

Figure 8:
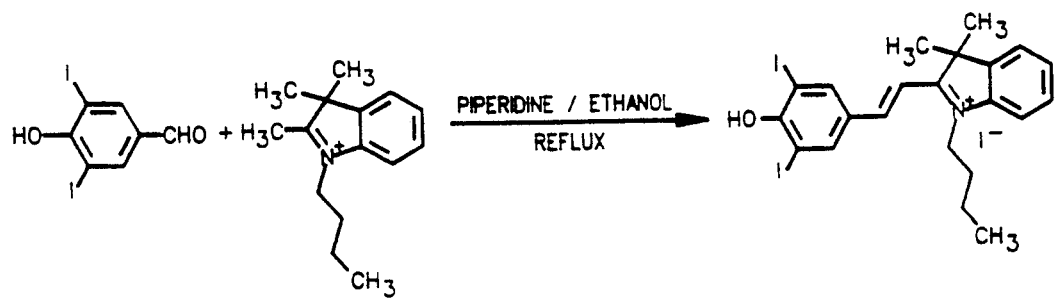

A mixture of 3,5-diiodo-4-hydroxy-benzaldehyde (3.73, 10 mmole), 1-(n-butyl)-2,3,3-trimethylindoleninium iodide (D.P. Maisuradze et al., *Soobschch. Akad. Nauk. Gruz. SSR* 50, 77-82 (1968): CA 69:106526r) (4.46 g, 13 mmole) and piperidine (0.8 ml) in EtOH (40 ml) was maintained under an inert gas atmosphere. The solution was refluxed for 1 hour, and cooled to an ambient temperature. The solution was evaporated in dryness in vacuo, leaving a residue. The residue was taken up on EtOH (10 ml) and treated with 1.93M HCl in i-PrOH (3.0 ml). The solution was thereafter again evaporated to dryness in vacuo, leaving a residue. The residue was taken up in EtOH (4 ml). The solution was refrigerated and crystals spontaneously formed. The crystalline solids that separated were collected by filtration, washed with ice-cold EtOH and vacuum dried to give crude 1-(n-butyl)-2-(4'-hydroxy-3',5'-diiodostyryl)-3,3-dimethylindoleninium iodide (4.90 g, 80.7%). The crude compound was taken up in hot EtOH (60 ml), filtered through paper and concentrated in vacuo to about 30 ml. The solution was allowed to crystallize. The crystal solids that separated were collected, washed and dried as above to provide the analytically pure compound 1-(n-butyl)-2-(4'-hydroxy-3',5'-diiodostyryl)-3,3-dimethylindoleninium iodide (3.90 g, 56%) as a bright orange powder. The above-described method for preparing the compound is generally illustrated by FIG. 8. Spectroscopic data identifying the compound is set forth below in Table 12.

Table 12

IR (KBr) cm$^{-1}$ 3361, 2979, 1605, 1574, 1530, 1463, 1402, 1372, 1320, 1250, 1213, 1198, 1136.

$^1$H NMR (DMSO-d$^6$)$\delta$ 8.63 (s, 2H), 8.23 (d, H=15.9 Hz, 1H), 7.39-7.87 (m, 6H), 4.65 (t, J=7.0, 2H), 1.73-1.85 (m, 2H), 1.76 (s, 6H), 1.34-1.48 (m, 2H), 0.93 (t, J=7.3 Hz, 3H).

$^{13}$C NMR (DMSO-d$^6$)ppm 181.2, 160.7, 150.9, 143.7, 141.7, 140.7, 129.8, 129.0, 123.0, 115.0, 110.4, 87.7, 52.0, 46.1, 30.4, 25.8, 19.2, 13.7 (4 coincident bands).

Analysis calculated for C$_{22}$H$_{24}$I$_3$NO·EtOH: C, 38.68; H, 4.06; N, 1.89. Found: C, 38.55; H, 3.96; N, 1.91.

Example 13

Comparison of the Dose Response of the Reagent Strips of the Present Invention and Albustix A urine pool with a specific gravity of 1.007, which was shown by immunoassay to be devoid of albumin, was spiked to various clinically significant levels with Pentex® human serum albumin (Miles Inc., Elkhart, Ind., USA). Using a Clinitek 200® Instrument (Miles Inc., Elkhart, Ind., USA) protein measurements were made using test strips including DIDNTB, SPDIB and a polypropylene glycol having a molecular weight of about 2000.

The reagent strips were prepared as follows. E&D 237 (Ahlstrom Filtration, Inc., Mount Holley Springs, Pa., USA) paper was dipped in a solution including a 0.5M citrate buffer pH 2.5 in 20% ethanol and 0.08 mM SPDIB. The strip was subsequently dipped in a second solution including 0.3 mM DIDNTB and 1% P-2000 (a polypropylene glycol having an average molecular weight of 2000 and available from Fluka Chemical Company under the tradename designation P-2000). The paper was then dried.

Figure 9:
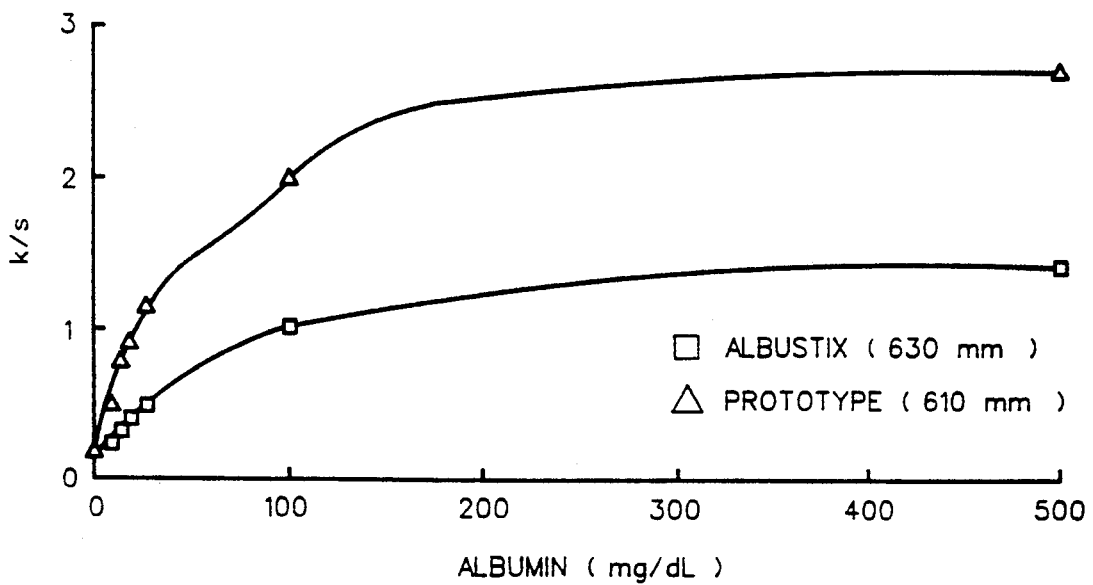
FIG. 9 illustrates dose response curves of analytical strips impregnated with 5',5"-dinitro-3',3"-diiodo-3,4,5,6-tetrabromophenolsulfonephthalein (DIDNTB), 1-(ω-sulfopropyl)-2-(4'-hydroxy-3',5'-diiodostyryl)-3,-3-dimethylindoleninium betaine (SPDIB) and a polypropylene glycol having a molecular weight of 2000 (-Δ-) [prototype], and Albustix (-□-)

Resolution was quantitatively expressed in delta K/S between albumin levels, as shown in FIG. 9. K/S are calculated from the formula:

$$K/S = \frac{(1-R)^2}{2R}$$

wherein R is the fraction of reflectance from the test device, K is a constant, and S is the light scattering coefficient of the particular reflecting medium. The above equation is a simplified form of the well-known Kubelka-Munk equation [See Gustav Kortum, "Reflectance Sepctroscopy," pp. 106–11, Springer Verlas, New York (1969)]. K/S was determined at 25 seconds.

The reagent strip prepared above and reagent strip available from Miles Inc., Elkhart, Ind., under the tradename designation Albustix, were compared for their response to the different levels of protein. The result of this comparison are summarized as FIG. 9. The strip of the invention was more sensitive to low levels of protein than Albustix. Furthermore, greater resolution between protein levels are seen with the invention.

Example 14

Figure 10:
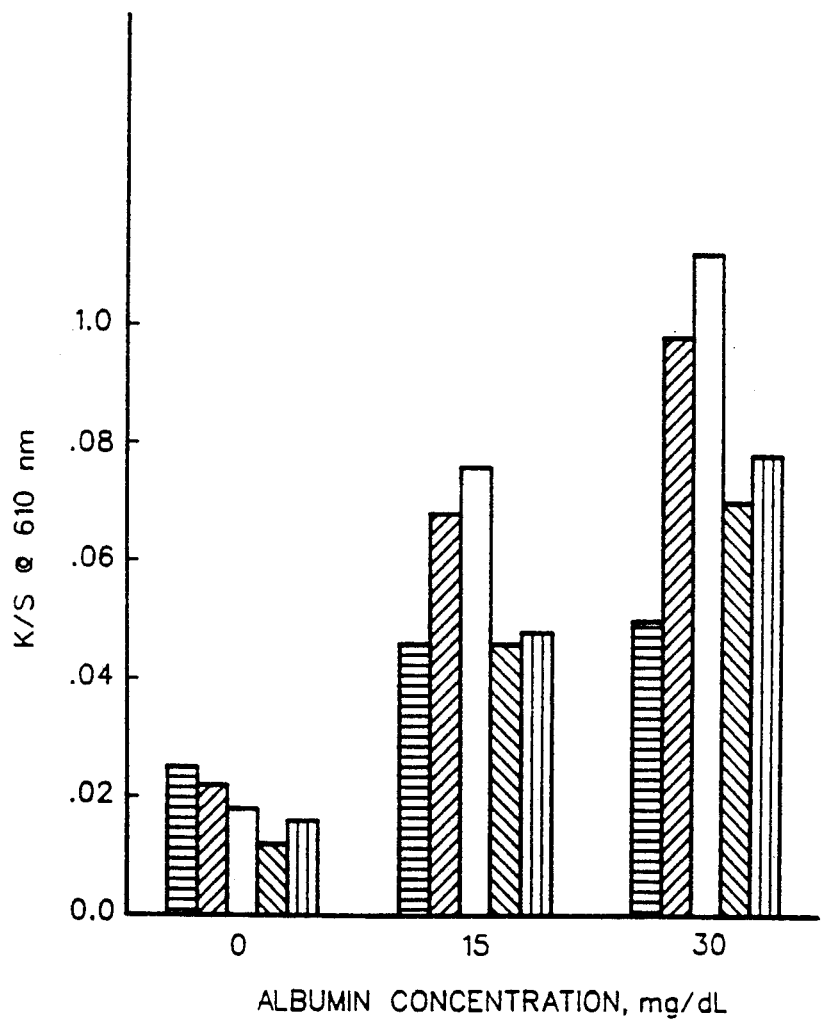
FIG. 10 is a bar graph illustrating the dose response of analytical test strips impregnated with DIDNTB and SPDIB alone (-▤-), DIDNTB, SPDIB and Fenoil D4030 (-▨-), DIDNTB, SPDIB and P-2000 (-□-), DIDNTB, SPDIB and KOK 10,071 (-▩-), and DIDNTB, SPDIB and Lutanol M40 (-▥-).

Comparison of Reagent Strips Including One of Several Selected Color Enhancing Polymers Using the same urine pool described above, measurements were made using test strips including DIDNTB and SPDIB, and no color enhancing polymer or one color enhancing polymers selected from the group consisting of Fenoil D4030, P-2000 (a polypropylene glycol having an average molecular weight of 2000 and available from Fluka Chemical Company under the tradename designation P-2000) KOK 10,071, and Lutonal M40. K/S was determined at 25 seconds. The data is summarized in FIG. 10.

The blank background color was decreased by Fenoil D4030, P-2000, KOK 10,071 and Lutonal M40. Fenoil D4030 and P-2000 caused a marked enhancement in dose response. From the data summarized in FIG. 10, the P-2000 would be the more preferred since it showed the greatest improvement in resolution between albumin concentrations. KOK 10,071, however, is also preferred since it lowers background coloration significantly.

Example 15

Reagent Strip Preparation

One method for the preparation of the urinary protein reagent strip discussed herein is shown below. The method described is a continuous method for mass producing urinary protein reagent test strips.

According to the method, a thin absorbent strip of paper is moved through the line at a preferred speed of about four feet per minute. One preferred paper being E&D 237. The paper is first dipped into a buffered bath, pH 2.5, including the merocyanine protein error indicator SPDIB dissolved in ethanol or another suitable organic solvent. The paper is subsequently dipped a second time in a bath containing the phenolsulfonephthalein protein error indicator DIDNTB dissolved in ethanol or another suitable organic solvent.

According to one preferred method, the first bath contains a 0.5M potassium citrate buffer, pH 2.5, 0.08 mM SPDIB in 20% ethanol, and the second bath includes 0.3M DIDNTB in ethanol, and a color enhancing polymer.

If a polypropylene glycol is used as the color enhancing polymer, the second ethanol bath should include one percent solution of polypropylene glycol. A preferred polypropylene glycol having a molecular average weight of about 2000 is available from Fluka Chemical Company under the tradename designation P-2000. If, however, a test paper is being manufactured which does not include a color enhancing polymer, the second dip includes only DIDNTB in ethanol.

The test strip is then passed through a dryer having an air pressure of one inch of water and a temperature of 60° C. at a speed of four feet per minute. The test strips are then cut and packaged.

Example 16

Reagent Strip Stabilized Against Thermal Stress

Heat stress induces substantial loss of reactivity in this reagent. It has been discovered adding sorbitol or glycerol to protein assay formulation containing polypropylene glycol increases stability toward heat stress. Improvements in response to thermal stress were also documented when polypropylene glycol was replaced with a different polymer, specifically Lutonal M40, a polyvinylisobutyl ether supplied by the BASF Company. Lastly, thermal stress stability was improved by replacing the citrate buffer commonly used in protein assays (test strips) with glycine. It has also been discovered that protein assays including the polymer Lutonal M40, also produce a reagent with increased resistance to interference by high specific gravity (SG) urines. The Lutonal M40 polymer was superior to polypropylene glycol in reducing this SG interference.

Stability data were obtained by testing the reagent strips with buffer solutions in the absence and presence of added albumin (HSA). The buffer contained 1% NaCl, 2.5% urea and 0.018M potassium phosphate, pH 7. The data are shown in the following Table 13. All reagents were prepared with Whatman CCP500 paper as described in Example 13 and contained 0.3 mM DIDNTB, 0.08 mM SPDIB, 0.625M buffer, in addition to the indicated components.

TABLE 13

LOSS IN NET REACTIVITY AFTER 4 WEEKS @ 50° C.
(compared to 4 week/20° C. or 4 week/26° C.)
WITH TESTING SOLUTIONS CONTAINING 30 mg/dL HSA

| Buffer | Polymer/Additive | % Loss in K/S Exp. 1 | Exp. 2 | Exp. 3 |
|---|---|---|---|---|
| Citrate pH 2.5 | P-2000 | 39 | 49 | 28 |
| Citrate pH 2.5 | P-2000/3% sorbitol | 9 | | |
| Citrate pH 2.5 | P-2000/1% glycerol | 13 | | |
| Citrate pH 2.5 | Lutonal M40 | | 0 | |
| Glycine pH 2.3 | P-2000 | | | 7 |

As indicated here, loss of reactivity with the polypropylene glycol P-2000 reagent ranged from 28 to 49%, and was lowered considerably by the addition of sorbitol or glycerol, or by replacing the citrate buffer. Such loss of reactivity was avoided completely by replacing the Polyproylene glycol P-2000 with the Lutonal I-30 polymer. Thus, sorbitol, glycerol, glycine and Lutonal I-30 are categorized for purposes of this invention as thermal stress reducing agents because they all improve the thermal stability of a protein assay when present in the formulation.

The superior performance of the Lutonal M40 reagent in minimizing the SG interference was shown with 13 clinical samples of SG ≧ 1.020 and found to be negative for proteninuria by the Sulfosal method. These samples were also test for total protein by the Coomassie blue (CBB) method and for albumin by immunoassay. The threshold for proteninuria is generally thought to be 15 mg/dl total protein and 3 mg/dl HSA. Thus, according to these criteria and to the Sulfosal results, these samples were below the proteninuria threshold and should be classified as negative. The results are shown in Table 14.

TABLE 14

| SG | HSA, mg/dL | CBB, mg/dL | Dual Indicator Reagent | |
|---|---|---|---|---|
| | | | P-2000/Sorbitol | Lutonal |
| 1.024 | 2.8 | 14.4 | yellow-green | NEG |
| 1.025 | 1.2 | 11.7 | yellow-green | NEG |
| 1.031 | 1.5 | 10.9 | NEG | NEG |
| 1.025 | 0.9 | 11.2 | NEG | NEG |
| 1.024 | 30 | 12.1 | yellow-green | NEG |
| 1.020 | 0.6 | 7.6 | NEG | NEG |
| 1.026 | 1.7 | 11.3 | NEG | NEG |
| 1.028 | 1.3 | 17.6 | green | NEG-Tr |
| 1.021 | 0.8 | 9.4 | green | NEG |
| 1.022 | 0.9 | 10.8 | green | NEG |
| 1.021 | 1.5 | 5.8 | NEG | NEG |
| 1.028 | 2.1 | 15.2 | green | NEG |
| 1.026 | 2.3 | 16.8 | green | NEG |

It is evident in this group of high SG samples that the Lutonal M40 reagent gave only one possible false trace, while the majority of the samples might have been traces with the P-2000 reagent. For example, the green color fell between the negative and trace block and could have been classified as either.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. An analytical test strip for the detection of protein in a biological sample comprising an absorbent carrier impregnated with a phenolsulfonephthalein protein error indicator and a merocyanine protein error indicator, the phenolsulfonephthalein protein error indicator is the compound:

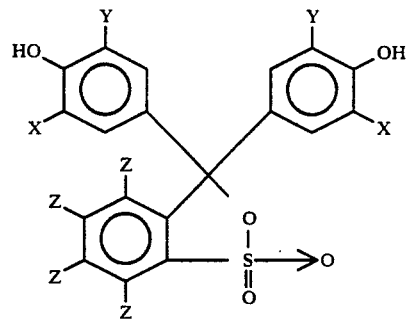

wherein:
X is —I, —Br or —Cl;
Y is —NO₂ or —NO; and
Z is —I, —Br or —Cl; and the merocyanine protein error indicator is in a concentration sufficient to produce a colorimetric change in the presence of protein wherein the compound is

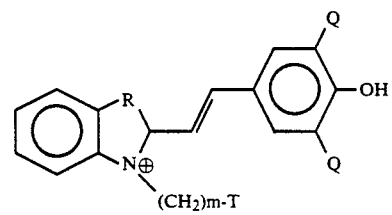

wherein:
m is an integer from 1 to 6;
Q is —Br, —I or Cl;
T is —SO$_3\theta$ or —H; and
R is S, Se, O or C(C$_n$H$_{2n+1}$)$_2$,
wherein:
n is an integer from 1 to 6.

2. The analytical test strip of claim 1 wherein X is —Br or —I; Y is —NO₂; Z is —Br; m is the integer 3 or 4; Q is —Br or —I; and R is C(C$_n$H$_{2n+1}$)$_2$, wherein n is an integer from 1 to 3; and T is —SO$_3\theta$.

3. The analytical test strip of claim 1 wherein X is —Br; Y is —NO₂; Z is —Br; Q is —I, m is the integer 3; and R is C(CH$_3$)$_2$.

4. The analytical test strip of claim 1 wherein the phenolsulfonephthalein protein error indicator and the merocyanine protein error indicator are included in the test strip in a molar ratio of from about 10 to 1 to about 1 to 1.

5. The analytical test strip of claim 1 wherein the phenolsulfonephthalein protein error indicator and the merocyanine protein error indicator are included in the test strip in a molar ratio of from about 5 to 1 to about 2 to 1.

6. The analytical test strip of claim 1 wherein the test strip further includes a buffer and color enhancing polymer.

7. The analytical test strip of claim 6 wherein the color enhancing polymer is polypropylene glycol having an average molecular weight of from about 1000 to about 4000.

8. An analytical test strip for the detection of protein in a biological sample comprising an absorbent carrier impregnated with a phenolsulfonephthalein protein error indicator and a merocyanine protein error indicator, the phenolsulfonephthalein protein error indicator is the compound:

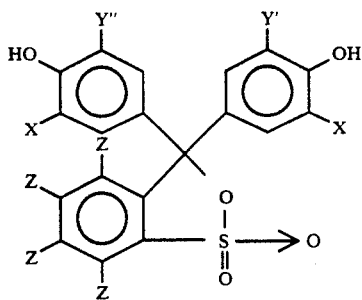

wherein:
X is —I, —Br or —Cl;
Y' is —NO₂ or —NO;
Y" is —I, —Br or —Cl; and
Z is —I, —Br or —Cl; and the merocyanine protein error indicator is in a concentration sufficient to produce a colorimetric change in the presence of protein wherein the compound is

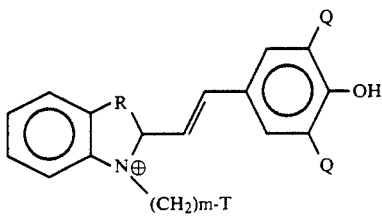

wherein:
m is an integer from 1 to 6;
Q is —Br, —I or Cl;
T is —SO₃θ or —H; and
R is S, Se, O or C(C$_n$H$_{2n+1}$)₂,
wherein:
n is an integer from 1 to 6.

9. The analytical test strip of claim 8 wherein X is —Br or —I; Y' is —NO₂; Y' is —Br or —I; Z is —Br; m is the integer 3 or 4; Q is —Br or —I; and R is C(C$_n$H$_{2n+1}$)₂, wherein n is an integer from 1 to 3; and T is —SO₃θ.

10. The analytical test strip of claim 8 wherein X is —Br; Y' is —NO₂; Y" is —I; Z is —Br; Q is —I, m is the integer 3; and R is C(CH₃)₂.

11. The analytical test strip of claim 8 wherein the phenolsulfonephthalein protein error indicator and the merocyanine protein error indicator are included in the test strip in a molar ratio of from about 10 to 1 to about 1 to 1.

12. The analytical test strip of claim 8 wherein the phenolsulfonephthalein protein error indicator and the merocyanine protein error indicator are included in the test strip in a molar ratio of from about 5 to 1 to about 2 to 1.

13. The analytical test strip of claim 8 wherein the test strip further includes a buffer, a thermal stress reducing agent and color enhancing polymer.

14. The analytical test strip of claim 13 wherein the color enhancing polymer is polypropylene glycol having an average molecular weight of from about 1000 to about 4000.

15. A method for the detection of protein in a biological sample, the method comprising the steps of:

(a) wetting an analytical test strip with the biological sample, the test strip including an absorbent carrier impregnated with a phenolsulfonephthalein protein error indicator and a merocyanine protein error indicator, the phenolsulfonephthalein protein error indicator is the compound:

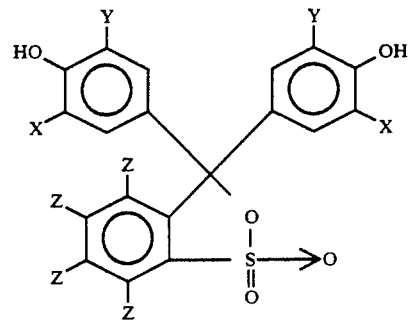

wherein:
X is —I, —Br or —Cl;
Y is —NO₂ or —NO; and
Z is —I, —Br or —Cl; and the merocyanine protein error indicator is in a concentration sufficient to produce a colorimetric change in the presence of protein wherein the compound is

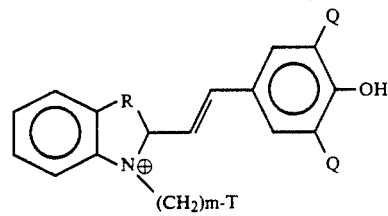

wherein:
m is an integer from 1 to 6;
Q is —Br, —I or Cl;
T is —SO₃θ or —H; and
R is S, Se, O or C(C$_n$H$_{2n+1}$)₂,
wherein:
n is an integer from 1 to 6;

(b) observing and recording any color change of the test strip, wherein a color change is indicative of protein in the biological sample.

16. A method for the detection of protein in a biological sample, the method comprising the steps of:

(a) wetting an analytical test strip with the biological sample, the test strip including an absorbent carrier impregnated with a phenolsulfonephthalein protein error indicator and a merocyanine protein error indicator, the phenolsulfonephthalein protein error indicator is the compound:

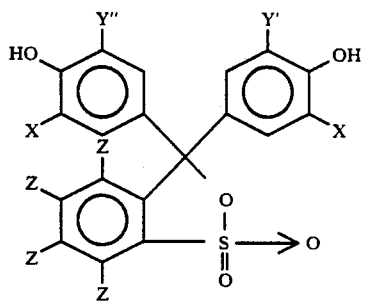

wherein:

X is —I, —Br or —Cl;

Y' is —NO₂ or —NO;

Y" is —I, —Br, or —Cl; and

Z is —I, —Br or —Cl; and the merocyanine protein error indicator is in a concentration sufficient to produce a colorimetric change in the presence of protein wherein the compound is

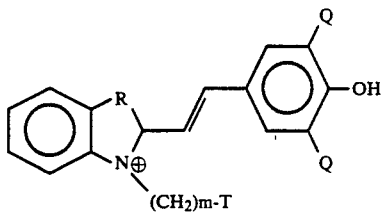

wherein
m is an integer from 1 to 6;
Q is —Br, —I or Cl;
T is —SO₃θ or —H; and
R is S, Se, O or $C(C_nH_{2n+1})_2$,
wherein:
n is an integer from 1 to 6; and (b) observing and recording any color change of the test strip, wherein a color change is indicative of protein in the biological sample.

17. The method of claim 16 wherein said test strip is further impregnated with a buffer and a color enhancing polymer.

18. The method of claim 16 wherein said test strip is further impregnated with glycine and a thermal stress reducing agent.

* * * * *